(12) United States Patent
Kojima (10) Patent No.: US 6,615,641 B2
(45) Date of Patent: Sep. 9, 2003

(54) STRUCTURE OF GAS SENSOR

(75) Inventor: Takashi Kojima, Kasugai (JP)

(73) Assignee: Denso Corporation, Kariya (JP)

(*) Notice: Subject to any disclaimer, the term of this patent is extended or adjusted under 35 U.S.C. 154(b) by 0 days.

(21) Appl. No.: 09/817,211

(22) Filed: Mar. 27, 2001

(65) Prior Publication Data

US 2001/0023612 A1 Sep. 27, 2001

(30) Foreign Application Priority Data

Mar. 27, 2000 (JP) .......................... 2000-085612
Feb. 8, 2001 (JP) .......................... 2001-032661

(51) Int. Cl.[7] ............................................. G01M 15/00
(52) U.S. Cl. ...................... 73/23.31; 73/23.32; 60/276
(58) Field of Search .......................... 73/1.06, 1.07, 73/23.31, 505, 516, 23.32; 204/400, 421–429; 60/276

(56) References Cited

U.S. PATENT DOCUMENTS 5,573,650 A * 11/1996 Fukaya et al. ............. 204/424
5,698,084 A    12/1997 Weyl et al.

FOREIGN PATENT DOCUMENTS

JP         11-242013        9/1999

* cited by examiner

Primary Examiner—Hezron Williams
Assistant Examiner—Monica D. Harrison
(74) Attorney, Agent, or Firm—Nixon & Vanderhye P.C.

(57) ABSTRACT

A gas sensor is provided which includes a first cylindrical insulation porcelain having a gas sensor element installed therein and a second cylindrical insulation porcelain disposed in contact with the first insulation porcelain. The first insulation porcelain is disposed on a seat surface formed on an inner wall of a housing through a packing ring. A contact between the first and second insulation porcelains being located within a contact permissible range defined by projecting outer and inner edges of the packing ring onto an end surface of the first insulation porcelain, thereby minimizing a lateral shift between the contact and the packing ring to avoid the breakage of the first insulation porcelain during assembly or use of the gas sensor.

6 Claims, 7 Drawing Sheets

STRUCTURE OF GAS SENSOR

BACKGROUND OF THE INVENTION

1. Technical Field of the Invention

The present invention relates generally to an improvement on a gas sensor which may be employed in an oxygen measuring device of an air-fuel ratio control system measuring an oxygen content in exhaust gasses of an internal combustion engine of automotive vehicles.

2. Background Art

For burning control of fuel in internal combustion engines, modern automotive vehicles use a gas sensor, e.g., an oxygen sensor which is installed in an exhaust system to measure the concentration of oxygen in exhaust gasses. A typical gas sensor of such a type includes a first insulation porcelain which is installed in a cylindrical housing and has disposed therein a sensing element and a second insulation porcelain abutting on the first insulation porcelain in alignment with the longitudinal center line of the housing. The first insulation porcelain rests on an annular step formed on an inner wall of the cylindrical housing through a packing ring. The second insulation porcelain is arranged in contact of an end with an end of the first insulation porcelain.

Usually, insulation porcelains are made of an insulating ceramic material. The ceramic is resistive to compression, but weak in tension. The ceramic is also subject to thermal expansion and shrinkage during baking, which may result in formation of waves on the surface thereof. This will cause a contact area between the ends of the first and second porcelains to be shifted laterally from the packing ring, thereby producing a bending stress (i.e., tensile stress) acting on the first insulation porcelain, which, in the worst case, leads to breakage of the first insulation porcelain.

For avoiding the above problem, Japanese Patent First Publication No. 11-242013 teaches a cushion which is disposed between the first and second insulation porcelains, however, this will result in increases in production process and cost.

SUMMARY OF THE INVENTION

It is therefore a principal object of the invention to avoid the disadvantages of the prior art.

It is another object of the invention to provide a gas sensor designed to minimize the breakage of an insulation porcelain during assembly and use of the gas sensor.

According to one aspect of the invention, there is provided a gas sensor which comprises: (a) a hollow cylindrical housing having a given length, the housing having a seat surface formed on an inner wall thereof: (b) a first insulation porcelain having a gas sensor element installed therein, the first insulation porcelain being disposed on the seat surface of the housing through a packing ring; and (c) a second insulation porcelain disposed in contact of an end surface thereof with an end surface of the first insulation porcelain, a contact between the first and second insulation porcelains being located within a contact permissible range defined by projecting outer and inner edges of the packing ring onto the end surface of the first insulation porcelain.

In the preferred mode of the invention, one of the first and second insulation porcelains has a protrusion formed on the end surface thereof to establish the contact between the first and second insulation porcelains.

One of the first and second insulation porcelains may have at least one ridge formed on the end surface thereof to establish line contact between the first and second insulation porcelains.

The contact permissible range may be defined by a width of the packing ring within an area ranging over an interval of the width of the packing ring from a center line middle between outermost and innermost edges of the packing ring in an inward direction of the gas sensor and an interval of the width of the packing ring from the center line in an outward direction of the gas sensor.

According to the second aspect of the invention, there is provided a gas sensor which comprises: (a) a hollow cylindrical housing having a given length, the housing having a seat surface formed on an inner wall thereof: (b) a first insulation porcelain having a gas sensor element installed therein, the first insulation porcelain being disposed on the seat surface of the housing through a packing ring; and (c) a second insulation porcelain disposed at an end surface thereof on an end surface of the first insulation porcelain at two contacts, a middle between the contacts being located within a contact permissible range defined by projecting outer and inner edges of the packing ring onto the end surface of the first insulation porcelains.

In the preferred mode of the invention, the contact permissible range may be defined by a width of the packing ring within an area ranging over an interval of the width of the packing ring from a center line middle between outermost and innermost edges of the packing ring in an inward direction of the gas sensor and an interval of the width of the packing ring from the center line in an outward direction of the gas sensor.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 7(*a*) is a partial enlarged view which shows arrangement of first and second porcelains according to the third embodiment of the invention;

FIG. 7(*b*) is a partial sectional view which shows a configuration of an end portion of a first porcelain.

DESCRIPTION OF THE PREFERRED EMBODIMENTS

Figure 1:
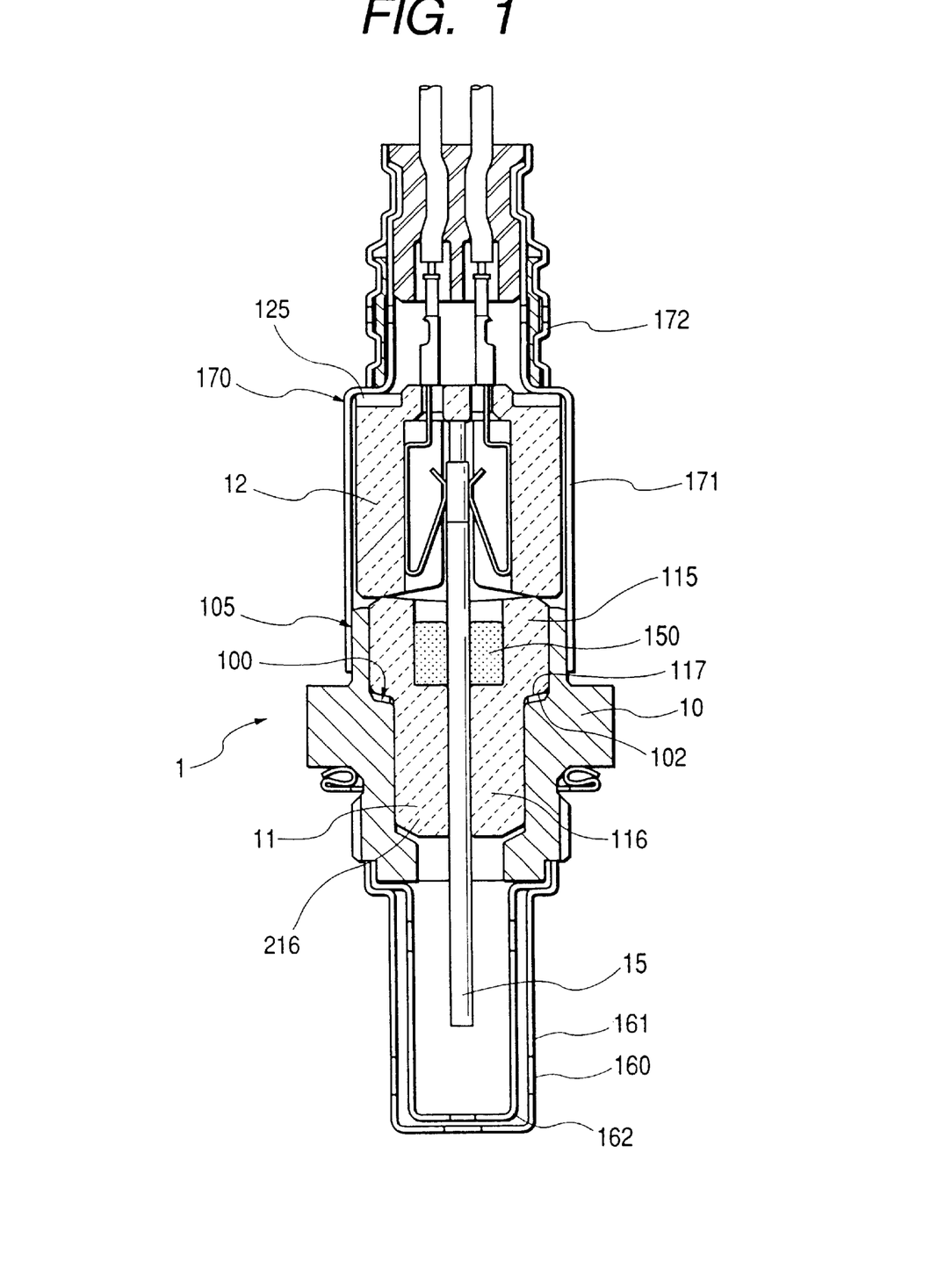
FIG. 1 is a vertical cross sectional view which shows a gas sensor according to the first embodiment of the invention.

Referring to the drawings, wherein like reference numbers refer to like parts in several views, particularly to FIG. 1, there is shown a gas sensor 1 according to the first embodiment of the invention which may be employed in an air-fuel ratio control system for automotive vehicles. Note that the present invention may be used with a variety of gas sensors such as $O_2$, HC, CO, and NOx sensors.

Figure 2:
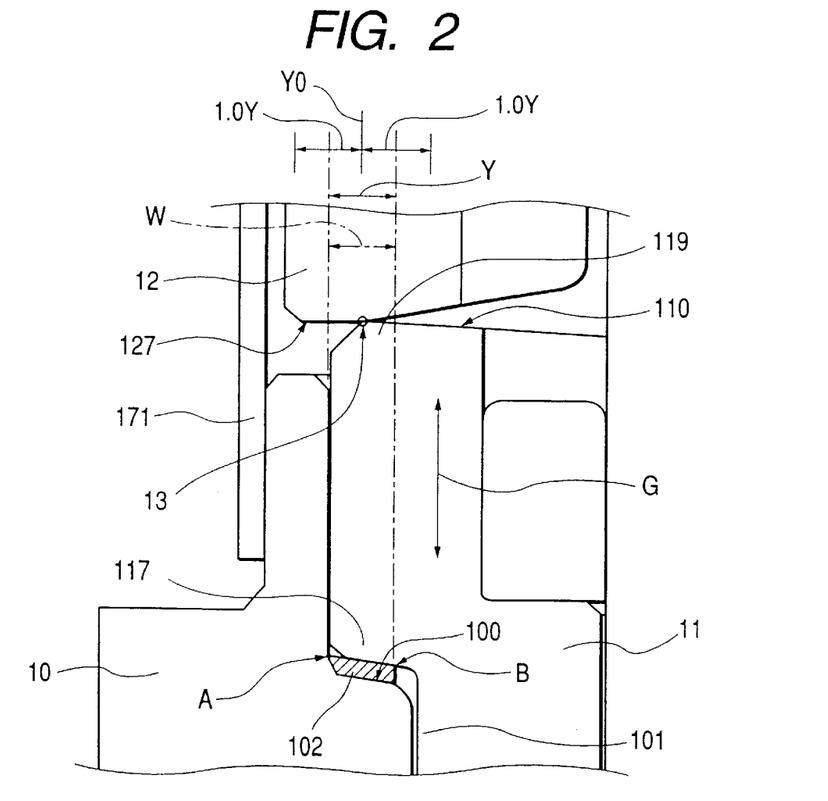
FIG. 2 is a partial enlarged view which shows arrangement of first and second porcelains.

The gas sensor 1 generally includes a hollow cylindrical housing 10, a sensor element 15, a first insulation porcelain 11, and a second insulation porcelain 12. The first and second insulation porcelains 11 and 12 are made of a ceramic material. The first insulation porcelain 11 retains therein the sensor element 15 and is installed within the housing 10 with a flange, as shown in FIG. 2, resting on an annular seat surface 100 formed on an inner wall 101 of the housing 10 through a packing ring 102. The second insulation porcelain 12 is disposed directly on a base end 110 of the first insulation porcelain 11 in line contact therewith.

Figure 3:
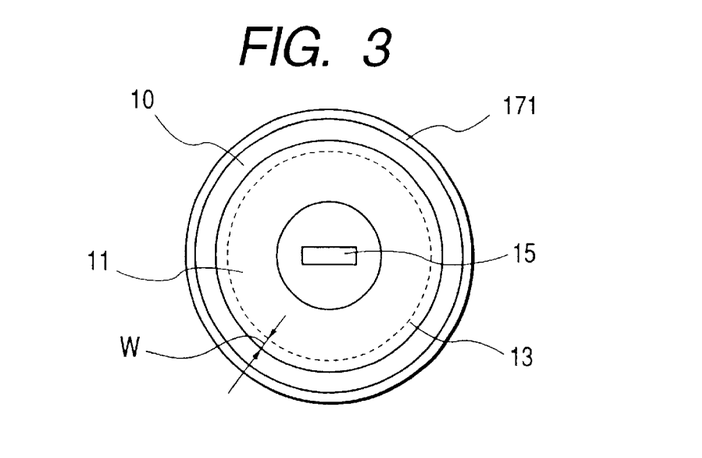
FIG. 3 is a lateral sectional view which shows the location of a line contact between first and second porcelains.

The line contact 13 is, as clearly shown in FIGS. 2 and 3, located within a range W defined by projecting an outermost edge A and an innermost edge B of the packing ring 102 in a longitudinal direction G of the gas sensor 1.

The gas sensor 1 also includes an outer cover 171, an outer protective cover 161, and an inner protective cover 162. The outer cover 171 is fitted on the housing 10 to cover the second insulation porcelain 12. The outer and inner protective covers 161 and 162 are installed on a head of the housing 10 and have formed therein a plurality of holes 160 through which a gas to be measured passes.

The first insulation porcelain 11 has, as described above, the annular seat surface 100 formed on the inner wall 101. The seat surface 100 is, as clearly shown in FIG. 2, oriented upward, as viewed in the drawing, in a longitudinal direction G of the gas sensor 1 and slightly inclined downward. The packing ring 102 made of a metallic plate is disposed on the seat surface 100. The first insulation porcelain 11 rests at a shoulder 117 on the packing ring 102.

The sensor element 15 is inserted into the first insulation porcelain 11. The sensor element 15 is made of a laminated plate such as one taught in U.S. Pat. No. 5,573,650, issued Nov. 12, 1996 to Fukaya et al., disclosure of which is incorporated herein by reference. A glass seal 150, as shown in FIG. 1 is fitted within the first insulation porcelain 11 to establish an airtight seal between the sensor element 15 and the inner surface of the first insulation porcelain 11.

The first insulation porcelain 11 is made of a ceramic cylinder having a circular horizontal cross section and has a large-diameter portion 115 and a small-diameter portion 116. The large-diameter portion 115 and the small-diameter portion 116 form therebetween the shoulder 117 which is, as described above, seated at the seat surface 100 of the housing 10.

The second insulation porcelain 12 is, as described above, disposed within the outer cover 171 on the base surface 110 of the first insulation porcelain 11. A disc spring 125 is installed between an inner surface of a shoulder 170 of the outer cover 171 and the end of the second insulation porcelain 12 to elastically urge the second insulation porcelain 12 against the first insulation porcelain 11.

The base end 110 of the first insulation porcelain 11, as clearly shown in FIG. 2, has an annular ridge 119 which forms the line contact 13 with the flat end surface 127 of the second insulation porcelain 12. The line contact 13 between the first and second insulation porcelains 11 and 13, as described above, lies within the range W. Instead of the annular ridge 119, an annular protrusion having a flat surface may alternatively be formed on the base end 110 to establish surface contact with the end surface 127 of the second insulation porcelain 12 within the range W. The line contact 13 and the surface contact are not limited to the annular configuration. For instance, a plurality of protrusions may be formed on either of the base end 110 of the first insulation porcelain 11 and the end surface 127 of the second insulation porcelain 12 to establish discrete points or surface contacts within the range W. This holds true of following embodiments as discussed later.

The operation and effects of this embodiment will be described below.

The location of the line contact 13 of the first and second insulation porcelains 11 and 12 within the range W serves to avoid a lateral shift between the line contact 13 and the packing ring 102 on which the first insulation porcelain 11 is held. This results in an decrease in bending stress acting on the first insulation porcelain 11, thereby minimizing the breakage of the first insulation porcelain 11 caused by undesirable impact during assembly or use of the gas sensor 1.

Figure 4:
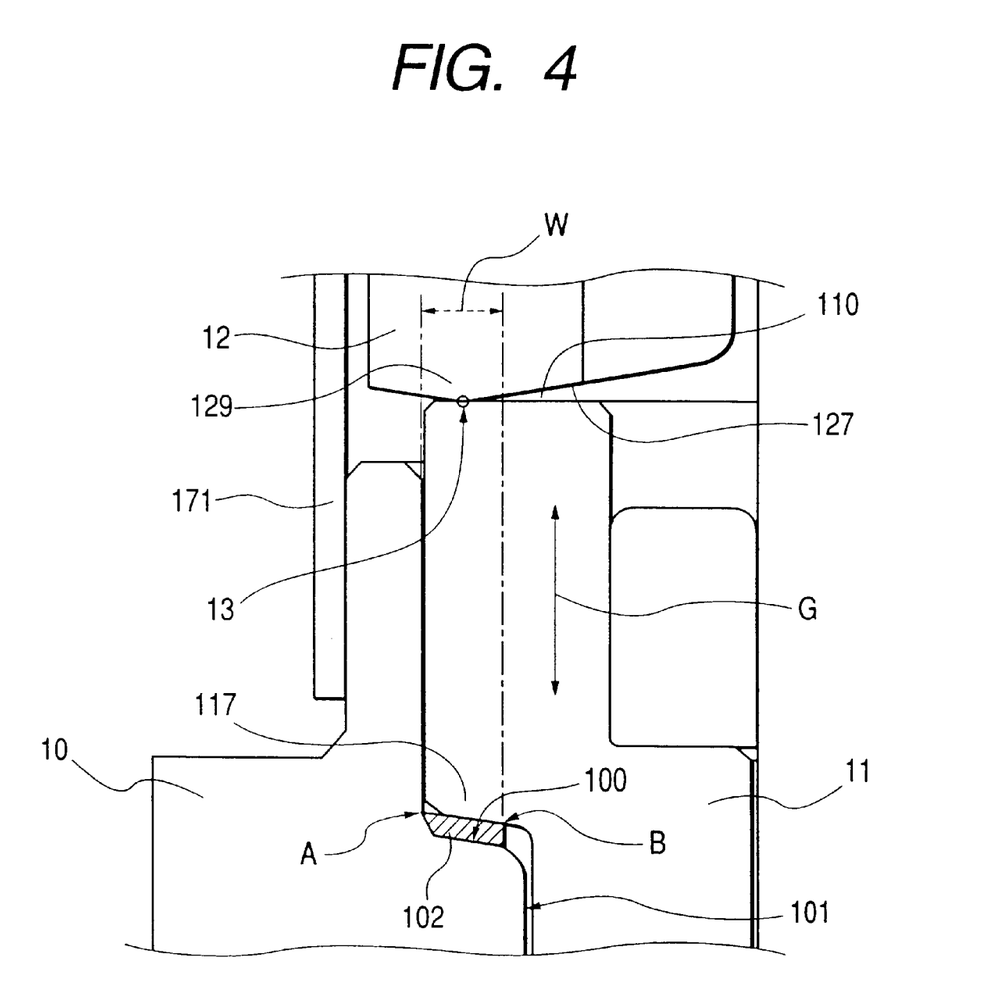
FIG. 4 is a partial enlarged view which shows a modification of the first embodiment.

The first insulation porcelain 11 has, as shown in FIG. 2, the annular ridge 119 formed on the base end 110, however, it may alternatively have, as shown in FIG. 4, the base end 110 flat, while the second porcelain 12 may have a similar ridge 129 formed on the end surface 127.

The contact permissible range W need not always be located exactly above the packing ring 102, as shown in FIG. 2, and may be defined inwardly or outwardly of the center circle Y0 middle between the outermost edge A and the innermost edge B of the packing ring 102 If the width of the packing ring 102 is defined as Y, the range W may be defined within an interval of 1.0 Y from the central circle Y0 in the inward or outward direction of the gas sensor 1. The same applies to the following embodiments.

Figure 5:
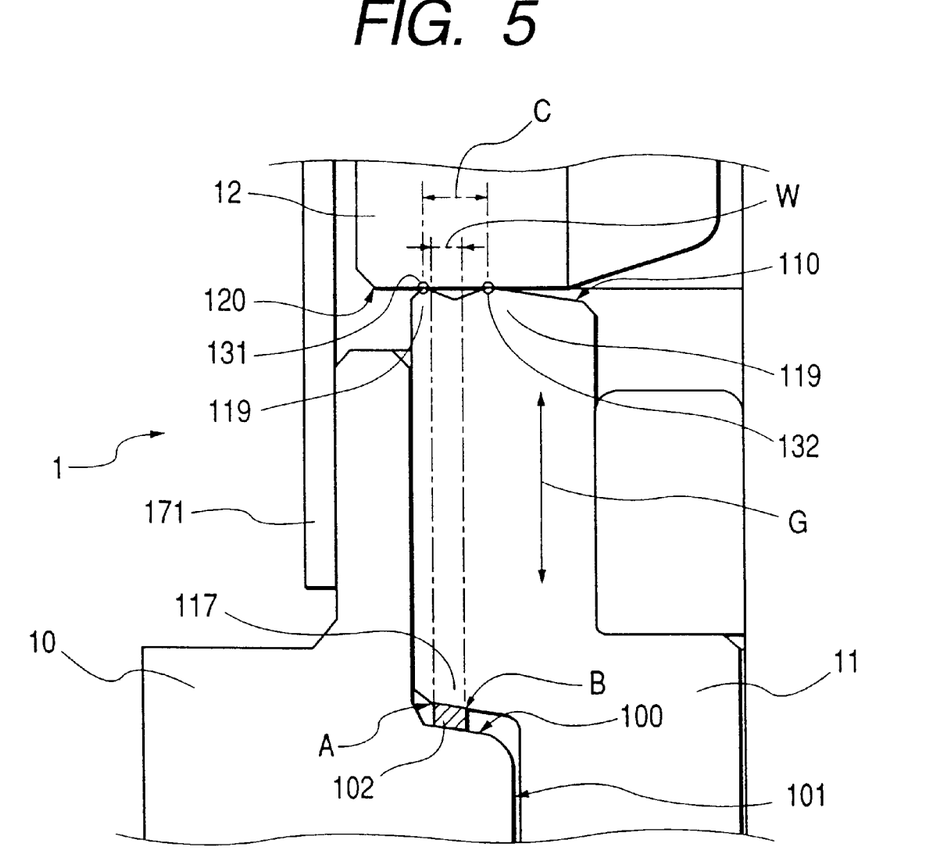
FIG. 5 is a partial enlarged view which shows arrangement of first and second porcelains according to the second embodiment of the invention.
Figure 6:
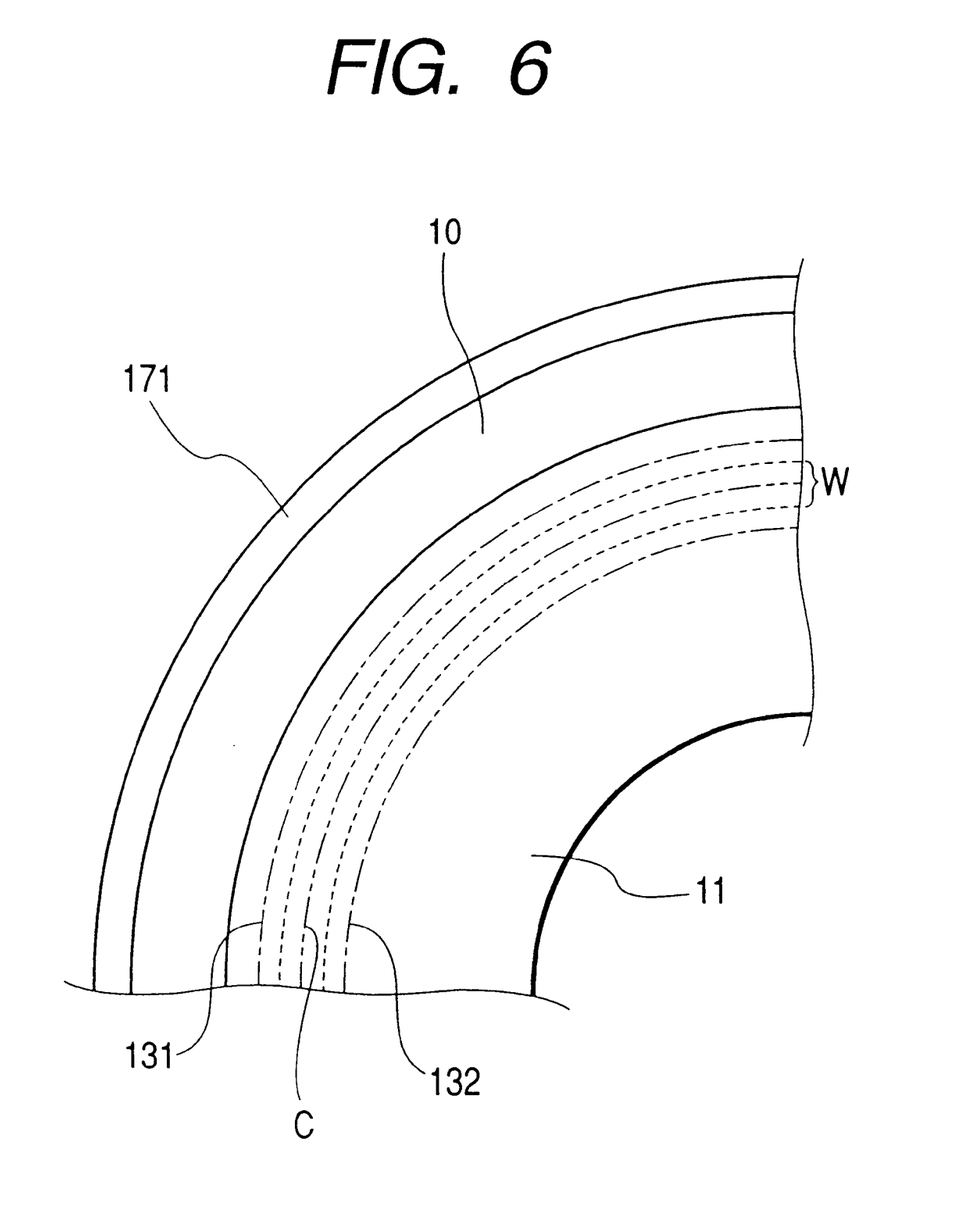
FIG. 6 is a partial lateral view which shows the location of line contacts between first and second porcelains.

FIGS. 5 and 6 show the second embodiment of the gas sensor 1.

The second insulation porcelain 12 has the flat end surface 120. The first insulation porcelain 11 has two annular ridges formed coaxially on the base end 110 to define, as shown in FIG. 6, line contacts 131 and 132 between the first and second insulation porcelains 11 and 12. The middle C between the first and second line contacts 131 and 132 lies within the range W.

The width of the packing ring 102 is smaller than that of the seat surface 100. The contact permissible range W is defined, like the first embodiment, by projecting the outermost edge A and the innermost edge B of the packing ring 102 in the longitudinal direction G of the gas sensor 1. The annular line contacts 131 and 132 are located outside the range W, while the middle C lies within the range W. This avoids, like the first embodiment, a lateral shift between the packing ring 102 on which the first insulation porcelain 11 is held and the line contacts 131 and 132 This results in an decrease in bending stress acting on the first insulation porcelain 11, thereby minimizing the breakage of the first insulation porcelain 11 caused by undesirable impact during assembly or use of the gas sensor 1.

Figure 7A:
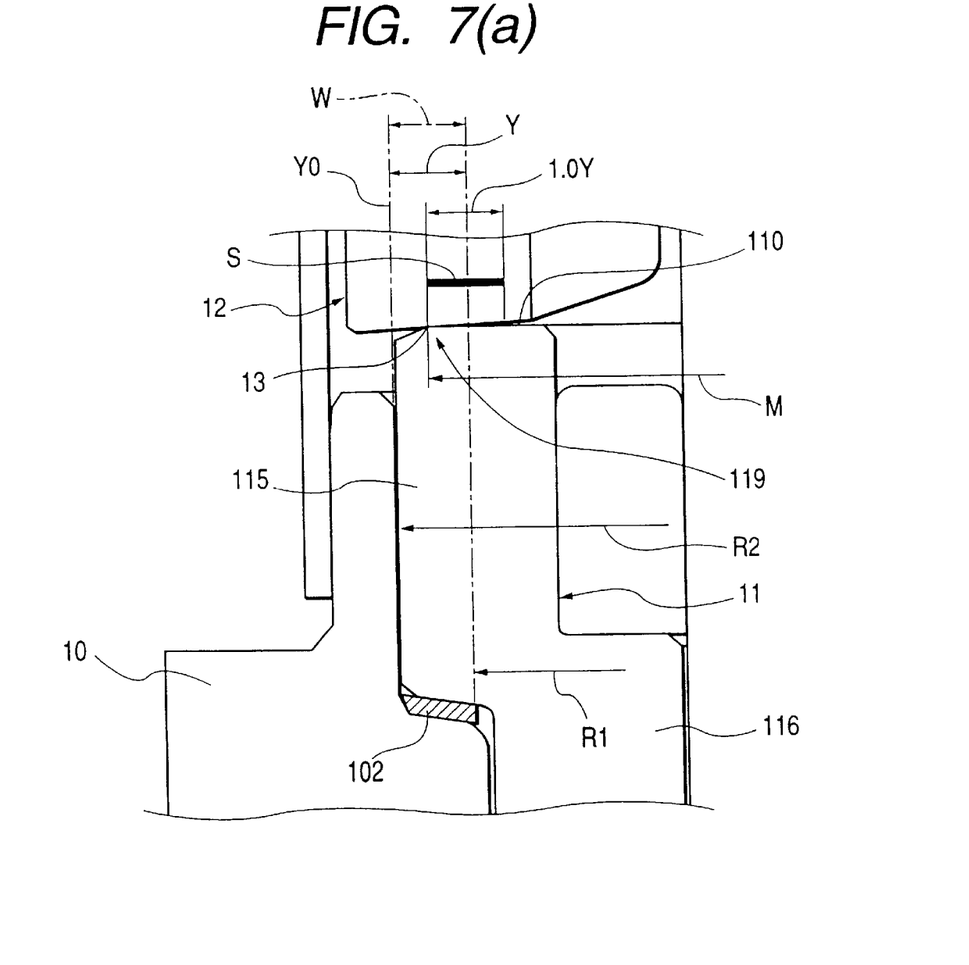
Figure 7B:
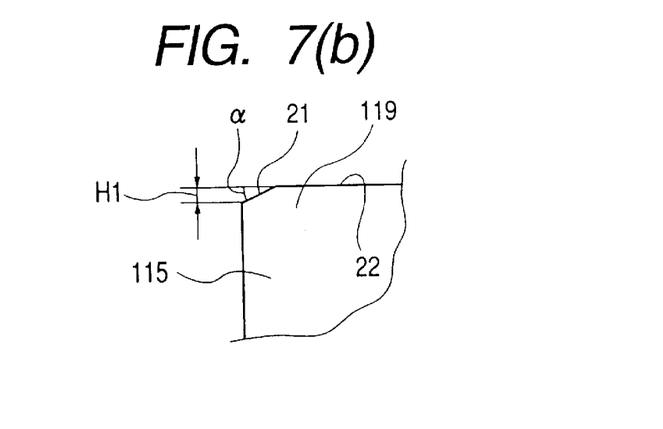

FIGS. 7(a) and 7(b) show the third embodiment of the gas sensor 1.

The packing ring 102 has an inner diameter R1 of 12 mm and an outer diameter R2 of 14.5 mm. The annular line contact 13 has a diameter M of 13 mm and lies within the range W defined, like the above embodiments, by projecting the outermost and innermost edges of the packing ring 102 along the longitudinal center line of the gas sensor 1.

The fist insulation porcelain 11 has the annular ridge 119 which is defined by a peripheral edge of the base surface 110. Specifically, the first insulation porcelain 11 has, as shown in FIG. 7(b), a central flat surface 22 extending substantially perpendicular to the longitudinal center line of the gas sensor 1 and a slant peripheral surface 21 formed outside of the central flat surface 22 inclined at an angle α of approximately 10° to the flat surface 22, thereby defining the annular ridge 119. The height H1 of the slant peripheral surface 21, i.e., the distance between the outer edge of the slant peripheral surface 21 and the outer edge of the central flat surface 22 is approximately 0.13 mm. In this embodiment, the contact permissible range W may be defined within an interval of 1.0Y, as indicated by S, from the central circle Y0 middle between the outermost and innermost edges of the packing ring 102.

Figure 8:
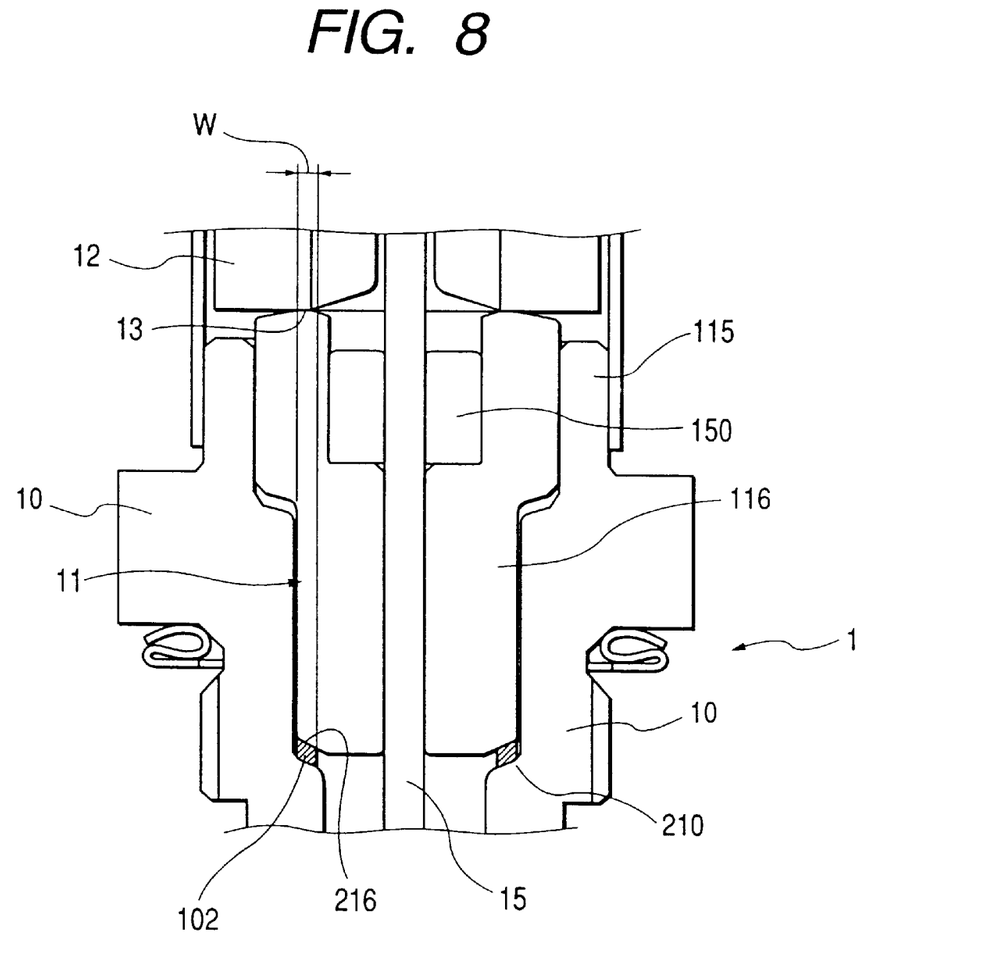
FIG. 8 is a partial vertical sectional view which shows a gas sensor according to the fourth embodiment of the invention.

FIG. 8 shows the fourth embodiment of the gas sensor 1.

The packing ring 102 need not be disposed between the shoulder 117 of the second insulation porcelain 12 and the seat surface 100 of the first insulation porcelain 11 and may be installed, as shown in FIG. 8, between a seat surface 210 formed on the inner wall of the housing 10 and an edge 216 of the head of the first insulation porcelain 11. The contact permissible range W is, similar to the above embodiments, defined by outermost and innermost edges of the packing ring 102.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor comprising:
  a hollow cylindrical housing having a given length, said housing having a seat surface formed on an inner wall thereof:
  a first insulation porcelain having a gas sensor element installed therein, said first insulation porcelain being disposed on the seat surface of said housing through a packing ring; and
  a second insulation porcelain disposed in contact of an end surface thereof with an end surface of the first insulation porcelain, a contact between said first and second insulation porcelains being located within a contact permissible range defined by projecting outer and inner edges of the packing ring onto the end surface of said first insulation porcelain.

2. A gas sensor as set forth in claim 1, wherein one of the first and second insulation porcelains has a protrusion formed on the end surface thereof to establish the contact between said first and second insulation porcelains.

3. A gas sensor as set forth in claim 1, wherein one of the first and second insulation porcelains has at least one ridge formed on the end surface thereof to establish line contact between said first and second insulation porcelains.

4. A gas sensor as set forth in claim 1, wherein the contact permissible range is defined by a width of the packing ring within an area ranging over an interval of the width of the packing ring from a center line middle between outermost and innermost edges of the packing ring in an inward direction of the gas sensor and an interval of the width of the packing ring from the center line in an outward direction of the gas sensor.

5. A gas sensor comprising:
  a hollow cylindrical housing having a given length, said housing having a seat surface formed on an inner wall thereof:
  a first insulation porcelain having a gas sensor element installed therein, said first insulation porcelain being disposed on the seat surface of said housing through a packing ring; and
  a second insulation porcelain disposed at an end surface thereof on an end surface of the first insulation porcelain at two contacts, a middle between the contacts being located within a contact permissible range defined by projecting outer and inner edges of the packing ring onto the end surface of said first insulation porcelains.

6. A gas sensor as set forth in claim 5, wherein the contact permissible range is defined by a width of the packing ring within an area ranging over an interval of the width of the packing ring from a center line middle between outermost and innermost edges of the packing ring in an inward direction of the gas sensor and an interval of the width of the packing ring from the center line in an outward direction of the gas sensor.

* * * * *